United States Patent
Meyer et al.

(10) Patent No.: US 8,109,883 B2
(45) Date of Patent: Feb. 7, 2012

(54) CABLE MONITORING APPARATUS

(75) Inventors: Peter F. Meyer, Shrewsbury, MA (US); Eliot Zaiken, Belchertown, MA (US)

(73) Assignee: Tyco Healthcare Group LP, Manfield, MA (US)

( * ) Notice: Subject to any disclaimer, the term of this patent is extended or adjusted under 35 U.S.C. 154(b) by 118 days.

(21) Appl. No.: 11/528,914

(22) Filed: Sep. 28, 2006

(65) Prior Publication Data

US 2008/0081954 A1   Apr. 3, 2008

(51) Int. Cl.
- *A61B 5/03* (2006.01)
- *A61B 5/00* (2006.01)
- *A61B 5/103* (2006.01)
- *A61B 5/117* (2006.01)

(52) U.S. Cl. ......... 600/528; 600/300; 600/587; 600/588
(58) Field of Classification Search .............. 600/528, 600/300, 587, 588
See application file for complete search history.

(56) References Cited

U.S. PATENT DOCUMENTS

| | | | |
|---|---|---|---|
| 3,752,151 A | 8/1973 | Robichaud | |
| 3,805,769 A | 4/1974 | Sessions | |
| 3,828,766 A | 8/1974 | Krasnow | |
| 3,868,946 A | 3/1975 | Hurley | |
| 3,888,240 A | 6/1975 | Reinhold, Jr. et al. | |
| 3,901,218 A | 8/1975 | Buchalter | |
| 3,998,213 A | 12/1976 | Price | |
| 4,027,664 A | 6/1977 | Heavner, Jr. et al. | |
| 4,034,854 A | 7/1977 | Bevilacqua | |
| 4,077,397 A | 3/1978 | Ellis et al. | |
| 4,256,118 A * | 3/1981 | Nagel | 600/546 |
| 4,353,372 A | 10/1982 | Ayer | |
| 4,378,021 A * | 3/1983 | Strand | 600/522 |
| 4,385,272 A | 5/1983 | Whitehead | |
| 4,498,480 A | 2/1985 | Mortensen | |
| 4,729,377 A | 3/1988 | Granek et al. | |
| 4,763,660 A | 8/1988 | Kroll et al. | |
| 4,781,200 A | 11/1988 | Baker | |
| 4,785,822 A | 11/1988 | Wallace | |
| 4,815,964 A | 3/1989 | Cohen et al. | |
| 4,909,260 A | 3/1990 | Salem et al. | |
| 4,947,846 A | 8/1990 | Kitagawa et al. | |
| 4,957,109 A | 9/1990 | Groeger et al. | |

(Continued)

FOREIGN PATENT DOCUMENTS

EP   0766946   4/1997

(Continued)

OTHER PUBLICATIONS

International Search Report EP07253850 dated Dec. 21, 2007.

(Continued)

*Primary Examiner* — Max Hindenburg
*Assistant Examiner* — Sean Dougherty
(74) *Attorney, Agent, or Firm* — Lisa E. Winsor, Esq.

(57) ABSTRACT

A cable monitoring apparatus includes a housing having an input interface adapted to electrically connect to one end of a medical cable and an output interface adapted to electrically connect to a medical monitoring apparatus. Signal processing circuitry is incorporated within the housing for receiving a medical signal from the medical cable via the input interface and for selectively passing the medical signal to the medical monitoring apparatus via the output interface when in a first mode of operation, and has application software for selectively testing functionality of the medical cable when in a second mode of operation.

25 Claims, 4 Drawing Sheets

U.S. PATENT DOCUMENTS

| | | | |
|---|---|---|---|
| 5,263,481 A | 11/1993 | Axelgaard | |
| 5,279,308 A | 1/1994 | DiSabito et al. | |
| 5,301,680 A * | 4/1994 | Rosenberg | 600/546 |
| 5,341,806 A | 8/1994 | Gadsby et al. | |
| 5,353,793 A | 10/1994 | Bornn | |
| 5,370,116 A | 12/1994 | Rollman et al. | |
| 5,373,852 A | 12/1994 | Harrison et al. | |
| 5,405,269 A | 4/1995 | Stupecky | |
| 5,427,111 A * | 6/1995 | Traub et al. | 600/508 |
| 5,442,940 A * | 8/1995 | Secker et al. | 600/483 |
| 5,494,032 A * | 2/1996 | Robinson et al. | 600/323 |
| 5,507,290 A | 4/1996 | Kelly et al. | |
| 5,511,553 A * | 4/1996 | Segalowitz | 600/508 |
| 5,546,950 A | 8/1996 | Schoeckert et al. | |
| 5,566,680 A | 10/1996 | Urion et al. | |
| 5,622,168 A | 4/1997 | Keusch et al. | |
| 5,685,303 A | 11/1997 | Rollman et al. | |
| 5,694,940 A | 12/1997 | Unger et al. | |
| 5,704,351 A | 1/1998 | Mortara et al. | |
| 5,724,025 A * | 3/1998 | Tavori | 340/573.1 |
| 5,743,859 A | 4/1998 | Wodlinger et al. | |
| 5,766,133 A | 6/1998 | Faisandier | |
| 5,785,664 A * | 7/1998 | Rosenberg | 600/588 |
| 5,813,979 A | 9/1998 | Wolfer | |
| 5,865,740 A | 2/1999 | Kelly et al. | |
| 5,865,741 A | 2/1999 | Kelly et al. | |
| 5,886,576 A | 3/1999 | Carlson | |
| 5,913,834 A | 6/1999 | Francais | |
| 5,916,159 A | 6/1999 | Kelly et al. | |
| 5,935,061 A * | 8/1999 | Acker et al. | 600/304 |
| 5,938,597 A | 8/1999 | Stratbucker | |
| 5,951,497 A | 9/1999 | Wallace et al. | |
| 5,984,879 A | 11/1999 | Wallace et al. | |
| 6,006,125 A | 12/1999 | Kelly et al. | |
| 6,032,064 A | 2/2000 | Devlin et al. | |
| 6,044,283 A * | 3/2000 | Fein et al. | 600/310 |
| 6,055,448 A | 4/2000 | Anderson et al. | |
| 6,066,093 A | 5/2000 | Kelly et al. | |
| 6,115,623 A | 9/2000 | McFee | |
| 6,122,536 A | 9/2000 | Sun et al. | |
| 6,157,851 A | 12/2000 | Kelly et al. | |
| 6,219,568 B1 | 4/2001 | Kelly et al. | |
| 6,219,569 B1 | 4/2001 | Kelly et al. | |
| 6,231,524 B1 | 5/2001 | Wallace et al. | |
| 6,232,366 B1 | 5/2001 | Wang et al. | |
| 6,240,323 B1 | 5/2001 | Calenzo, Sr. et al. | |
| 6,339,720 B1 | 1/2002 | Anzellini et al. | |
| 6,360,119 B1 | 3/2002 | Roberts | |
| 6,400,977 B1 | 6/2002 | Kelly et al. | |
| 6,450,958 B1 * | 9/2002 | Linkhart et al. | 600/437 |
| 6,453,186 B1 | 9/2002 | Lovejoy et al. | |
| 6,456,872 B1 | 9/2002 | Faisandier | |
| 6,553,246 B1 | 4/2003 | Wenger | |
| 6,564,079 B1 | 5/2003 | Cory et al. | |
| 6,611,705 B2 | 8/2003 | Hopman et al. | |
| 6,623,312 B2 | 9/2003 | Merry et al. | |
| 6,647,286 B1 | 11/2003 | Kato et al. | |
| 6,654,626 B2 | 11/2003 | Devlin et al. | |
| 6,748,797 B2 | 6/2004 | Breed et al. | |
| 6,751,493 B2 | 6/2004 | Wenger | |
| 6,816,744 B2 | 11/2004 | Garfield | |
| 6,970,731 B1 | 11/2005 | Jayaraman et al. | |
| 6,973,341 B2 | 12/2005 | Watson | |
| 6,973,343 B2 | 12/2005 | Wenger | |
| 6,980,852 B2 | 12/2005 | Jersey-Willuhn et al. | |
| 7,104,801 B1 | 9/2006 | Brodnick et al. | |
| 7,144,372 B2 | 12/2006 | Ng et al. | |
| 7,150,655 B2 | 12/2006 | Mastrototaro et al. | |
| 7,169,107 B2 | 1/2007 | Jersey-Willuhn et al. | |
| 7,184,820 B2 | 2/2007 | Jersey-Willuhn et al. | |
| 7,197,357 B2 | 3/2007 | Istvan et al. | |
| 7,272,428 B2 | 9/2007 | Hopman et al. | |
| 7,333,850 B2 | 2/2008 | Marossero et al. | |
| 2002/0133069 A1 | 9/2002 | Roberts | |
| 2002/0188216 A1 | 12/2002 | Kayyali et al. | |
| 2004/0073127 A1 | 4/2004 | Istvan et al. | |
| 2004/0127802 A1 | 7/2004 | Istvan et al. | |
| 2004/0176674 A1 | 9/2004 | Nazeri | |
| 2005/0177052 A1 | 8/2005 | Istvan et al. | |
| 2005/0182466 A1 * | 8/2005 | Mahajan | 607/116 |
| 2005/0203349 A1 * | 9/2005 | Nanikashvili | 600/300 |
| 2006/0073728 A1 | 4/2006 | Zaiken et al. | |
| 2007/0038057 A1 | 2/2007 | Nam et al. | |
| 2007/0260133 A1 | 11/2007 | Meyer | |

FOREIGN PATENT DOCUMENTS

WO      WO 03/028550      4/2003

OTHER PUBLICATIONS

Andreas Boos et al.; "A New Lightweight Fetal Telemetry System"; Dec. 1995; Hewlett-Packard Journal; pp. 82-93.

* cited by examiner

CABLE MONITORING APPARATUS

BACKGROUND

1. Technical Field

The present disclosure relates to medical equipment. In particular, the present disclosure relates to a cable monitoring apparatus which checks the functionality of an electrical cable adapted to connect to a medical apparatus, such as a fetal monitor.

2. Description of Related Art

Fetal monitors have been widely used and are capable of measuring a wide variety of uterine, fetal and maternal parameters, such as for example, uterine temperature, intrauterine pressure, fetal electrocardiogram, etc. This information may be gathered via a variety of sensors (e.g., electrode arrays, pressure transducers, catheters, etc.) applied to the maternal patient. Monitoring signals, from the fetus and maternal patient, are received by the sensors, transmitted via electrical cables to a fetal monitor and displayed on the fetal monitor.

Typically, during labor and delivery, a multitude of sensors are required to receive monitoring signals containing maternal and fetal information. Application of maternal and fetal sensors is time consuming and at times unpleasant to the woman, particularly the application of invasive devices such as an intrauterine pressure transducer or a fetal scalp electrode. The proper operation of sensors is essential and clinicians continually monitor the various sensors and the associated systems to check functionality and to insure the sensors are providing accurate information.

When a sensor is not functioning properly or not providing accurate information, it becomes necessary to troubleshoot the entire fetal monitoring system to determine the origin of the malfunction. One troubleshooting step includes determining if the origin of the malfunction is hardware related, in particular a faulty sensor and/or electrical cable. Typically, electrical cables are easier to diagnose and replace since electrical cable replacement usually does not require the removal and reapplication of the sensor. Reusable cables may cost much more than disposable sensors, making the potentially unnecessary replacement of cables wasteful. Therefore, there is a need for a cable monitoring apparatus for determining whether the fetal monitoring cables are functioning properly.

SUMMARY

The present disclosure relates to medical equipment. In particular, the present disclosure relates to a cable monitoring apparatus which checks the functionality of an electrical cable adapted to connect to a medical apparatus, such as a fetal monitor, as well as allows for zeroing and/or re-zeroing of monitoring functions of the medical apparatus, wherein monitoring signals are supplied from fetal and maternal monitoring sensors.

In accordance with one preferred embodiment, a cable monitoring apparatus includes a housing having an input interface, adapted to electrically connect to one end of a medical cable, and an output interface adapted to electrically connect to an electrical system. Signal processing circuitry is incorporated within the housing for receiving a medical signal from the medical cable via the input interface and for selectively passing the medical signal to the electrical system via the output interface when in a first mode of operation, and has application software for selectively testing the functionality of the medical cable when in a second mode of operation.

The medical signal may include at least one monitoring signal selected from a group consisting of fetal and maternal medical signals. Preferably, the at least one monitoring signal is generated from a medical device selected from a group consisting of at least one medical electrode, a medical electrode sensor array, an abdominal strain gauge, a tocodynamometer, an intrauterine pressure catheter, an ultrasound transducer, a vacuum pressure sensor, a pulse oximeter, a pH sensor, a cervical dilation sensor, a cervical effacement sensor, a cervical length sensor, a fetal station sensor, and an ultrasound transducer.

The housing may include a cable diagnostic interface adapted to electrically connect with the remaining end of the medical cable whereby the software of the signal processing circuitry tests the functionality of the medical cable when in the second mode of operation. The housing includes at least one indicator for indicating an operating parameter corresponding to functionality of the medical cable. The housing may include first and second input interfaces for electrical connection to respective first and second medical cables.

The signal processing circuitry may be adapted to process the at least one monitoring signal when in the first mode of operation and provide an output signal indicative of an operating parameter of the at least one monitoring signal. The output signal may correspond to one of uterine activity or ECG activity. The housing may also include an output signal indicator associated with the output signal for displaying a condition of the output signal. The output signal indicator may be one of a visual or an audible alarm.

The signal processing circuitry may be further configured to perform a zero/re-zero function wherein the at least one monitoring signal is short-circuited to create a zero voltage signal. The signal processing circuitry is adapted to short circuit the at least one monitoring signal for a predetermined period of time. An indicator may be provided for indicating that the at least one monitoring signal is short-circuited.

Alternatively, a signature signal transmitter may be adapted to transmit a signature signal through the medical cable to a patient. The signature signal may be identifiable by the signal processing circuitry to determine the functionality of the medical cable.

In accordance with another embodiment, a cable monitoring system includes a cable monitor operable between a first and a second mode of operation wherein the first mode of operation selectively passes at least one monitoring signal from a medical device to a monitoring apparatus, and wherein the second mode of operation determines the functionality of an electrical cable. The at least one monitoring signal may be selected from a group consisting of fetal and maternal medical signals. A first input receives the at least one monitoring signal and a first output selectively passes the at least one monitoring signal to the monitoring apparatus. A diagnostic input may be provided whereby, in the second mode of operation, one end of the medical cable is connected to the first input and a second end of the medical cable is connected to the diagnostic input to thereby determine the functionality of the electrical cable. Signal processing circuitry is adapted to selectively pass the at least one monitoring signal from the medical device to the monitoring apparatus and to determine the functionality of the electrical cable.

In accordance with another embodiment, a method for fetal monitoring is disclosed. A medical cable monitor is electrically connecting with a fetal monitoring apparatus. One end of a medical cable is electrically connecting to an input interface of the medical cable monitor. In one mode of operation, the other end of the medical cable is electrically connected to a cable diagnostic interface of the cable monitor. In this mode of operation, signal processing circuitry of the medical cable monitor tests the functionality of the medical cable connected between the input interface and the cable diagnostic interface. In another mode of operation one end of medical cable is electrically connected to a sensor. The sensor senses maternal or fetal parameters and sends a maternal or fetal monitoring signal associated with the maternal or fetal parameters to the input of the medical cable monitor. Signal processing circuitry of the medical cable monitor passes the fetal monitoring signal to the fetal monitor.

In the step of connecting one end of the medical cable to a sensor, a sensor is selected from a group consisting of a medical electrode, a medical electrode sensor array, an abdominal strain gauge, a tocodynamometer, an intrauterine pressure catheter, a vacuum pressure sensor, a pulse oximeter, a pH sensor, a cervical dilation sensor, a cervical effacement sensor, a cervical length sensor, a fetal station sensor, and an ultrasound transducer.

DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
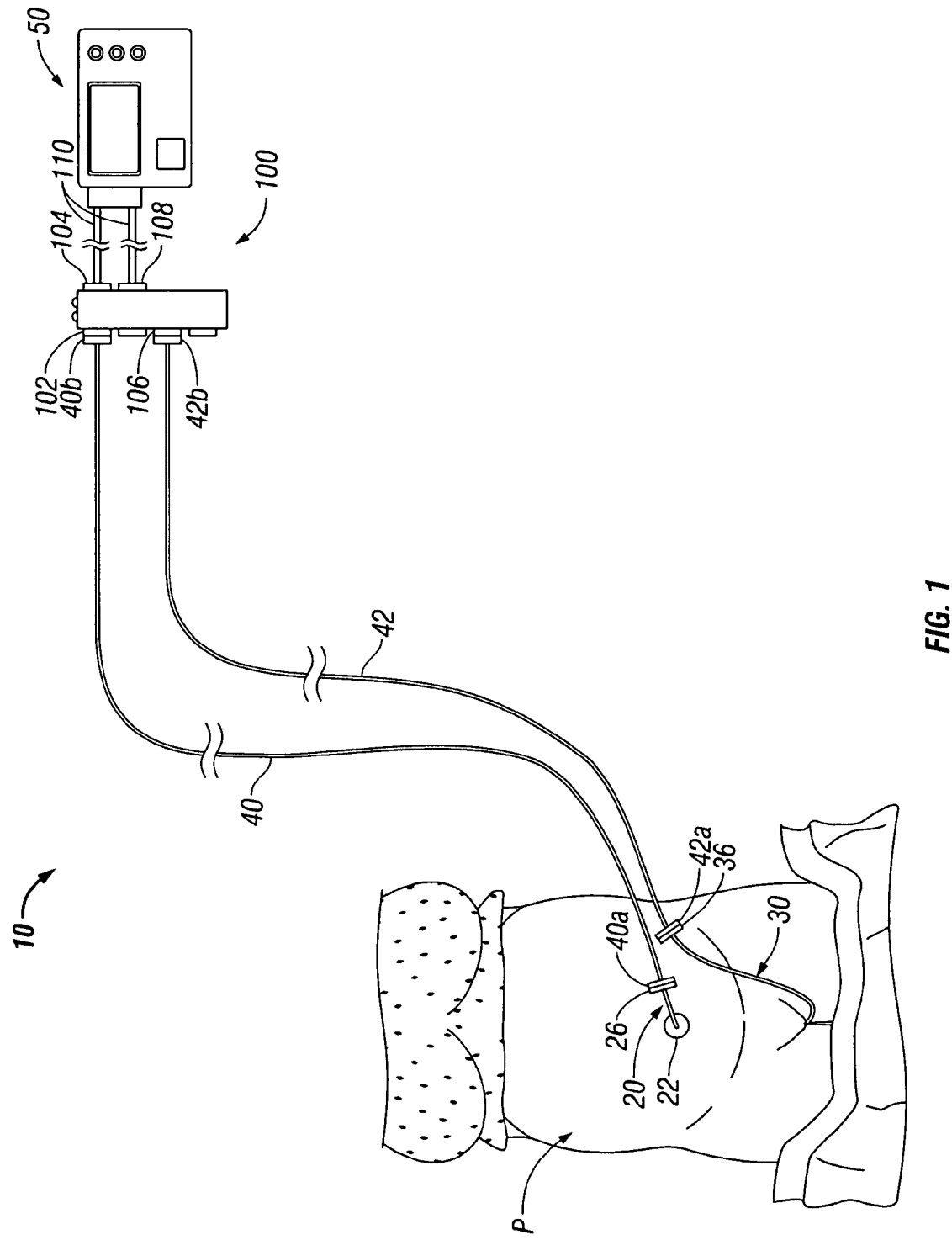
FIG. 1 is a view of a fetal monitoring system incorporating a cable monitoring apparatus in accordance with the present disclosure.

FIG. 1 shows a fetal monitoring system 10 incorporating a cable monitoring apparatus according to the present disclosure. The fetal monitoring system 10 includes one or more sensor, devices or probes, such as fetal electrocardiogram (FECG) sensor 20 and an intrauterine pressure (IUP) catheter 30. The FECG sensor 20 may include at least one electrode adapted to adhere to skin on the abdomen of the patient P. The IUP catheter 30 may be a pressure catheter placed within the uterus of the patient P. The FECG sensor 20 and the IUP catheter 30 are operably and electrically coupled with the FECG sensor cable connector 26 and IUP catheter cable connector 36, respectively.

In the discussion which follows, the term cable may incorporate a single conductor or may comprise an assembly of conductors arranged in any mode of operation known in the art. Connector refers to a single plug, receptacle, or other device capable of electro-mechanically connecting to a cable, device or apparatus. A connector assembly refers to the connection between two connectors wherein the connectors facilitate connectivity between two cables, devices or apparatus, or any combination thereof. Connection between the two components may be solely electrical without any mechanical means of connection. Such electrical connection may be infrared or incorporate electromagnetic wave principles. Thus, the term "connection" or "electrical connection" is to be construed as any electrical, mechanical connection or combination thereof known in the art.

The FECG electrical cable 40 and the IUP electrical cable 42 first connectors 40A, 42A are connected to the respective device connectors 26, 36. In the prior art, second connectors 40B, 42B of the cables 40, 42 connect directly to the monitoring device 50. Signal loss at the monitoring device 50 typically resulted in the replacement of an electrical cable 40, 42 since cable replacement is easier than the removal and subsequent reapplication of a sensor 20,30.

The first embodiment of a cable monitoring apparatus 100 in accordance with the present disclosure will now be discussed. Cable monitoring apparatus 100 is coupled between one or more electrical cables 40, 42 and the monitoring device 50. The FECG electrical cable second connector 40B of the FECG sensor cable 40 electro-mechanically connects to the first input connector 102 and the sensed information from the FECG sensor 20 is selectively passed through the first output connector 104 to the monitoring device 50. The IUP sensor cable second connector 42B of the IUP sensor cable 42 electro-mechanically connects to the second input connector 106 and the sensed information from the IUP sensor 30 is selectively passed through the second output connector 108 to a monitoring device 50. Cable monitoring apparatus 100 electro-mechanically connects to the monitoring device 50 with two interface cables 110. It is envisioned that the cable monitoring apparatus 100 electro-mechanically connects to the monitoring device in any number of ways known in the art.

FIG. 1 illustrates a fetal monitoring system 10 with a cable monitoring apparatus 100 interfacing with two sensor cables 40, 42 and one monitoring device 50. Monitoring device 50 may be a fetal monitoring device or any other device capable of receiving and displaying a monitoring signal. The present disclosure may interface with any number of cables or monitoring devices.

In a first mode of operation of cable monitoring apparatus 100, sensed information is passed from the sensors 20, 30 through the cables 40, 42 and the cable monitoring apparatus 100 and to the monitoring device 50. In a first mode of operation, cable monitoring apparatus 100 does not substantially alter or degrade the signal provided to the fetal monitoring system 10.

Figure 2:
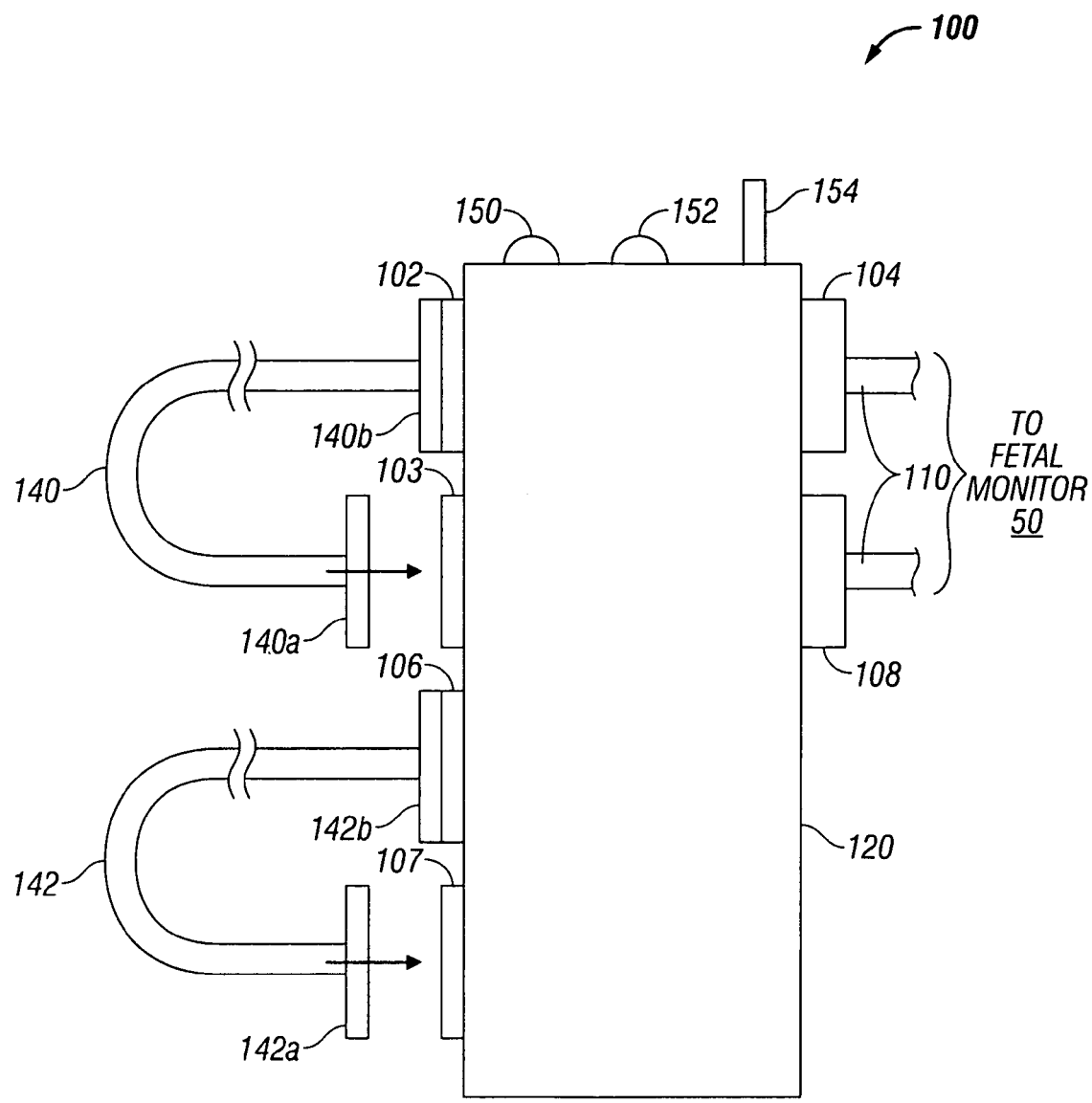
FIG. 2 is a view of the cable monitoring apparatus of FIG. 1.

With reference to FIG. 2, cable monitoring apparatus 100 consists of a housing 120 which houses a plurality of connectors and user interface devices described hereinbelow. In this particular embodiment, cable monitoring apparatus 100 is configured to connect to two medical sensors although it is envisioned cable monitoring apparatus 100 described herein may connect to any number of medical sensors or devices. Housing 120 may be sufficiently small and manufactured from lightweight materials, such as plastic, such that the cable monitoring apparatus 100 is a light-weight inline device.

FIG. 2 illustrates the cable monitoring apparatus 100 in a second mode of operation wherein cable monitoring apparatus 100 is utilized in a diagnostic capacity. Clinicians start the process of troubleshooting after it is determined that the fetal monitoring system 10 is not operating correctly. The cable monitoring apparatus 100 may be used as a diagnostic tool to determine the functionality of electrical cables 140, 142. The cable monitoring apparatus 100 may perform a number of diagnostic tests known in the art.

Second connector 140B of an electrical cable 140 is electro-mechanically connected to the first input connector 102. The first connector 140A of the same electrical cable 140 is disconnected from a medical sensor and electro-mechanically connected to the first diagnostic connector 103. A second electrical cable 142 may connect in a similar fashion with the second connector 142B connected to a second input connector 106 and the first connector 142A connected to a second diagnostic connector 107. The various electrical cables 140, 142 attached to the cable monitoring apparatus 100 may operate independent of each other wherein an electrical cable may be arranged in the first mode of operation while a second electrical cable may be arranged in the second mode of operation.

With reference to FIGS. 1 and 2, switching from the first mode of operation, as shown in FIG. 1 wherein sensed information is selectively passed through the cable monitoring apparatus, to the second mode of operation, as shown in FIG. 2 wherein the cable monitoring apparatus is used to diagnose an electrical cable, requires disconnecting the first connectors 140A, 142A of the first and second electrical cables 40, 42 from the FECG sensor cable connector 26 and the IUP catheter cable connector 36 and reconnecting the first connectors 140A, 142A to the first and second diagnostic connectors 103, 107.

Alternatively, the clinician may diagnose the electrical cable with cable monitoring apparatus 100 prior to connecting the first connectors 140A, 142A to the sensors connectors 26, 36.

Returning to FIG. 2, first cable indicator 150 indicates the functionality of a cable connected between the first input connector 102 and the first diagnostic connector 103. Second cable indicator 152 indicates the functionality of a cable connected between the second input connector 106 and the second diagnostic connector 107. First and second cable indicators 150, 152 may be audio indicators, visual indicators, or any indicator known in the art, or combination thereof.

Figure 3:
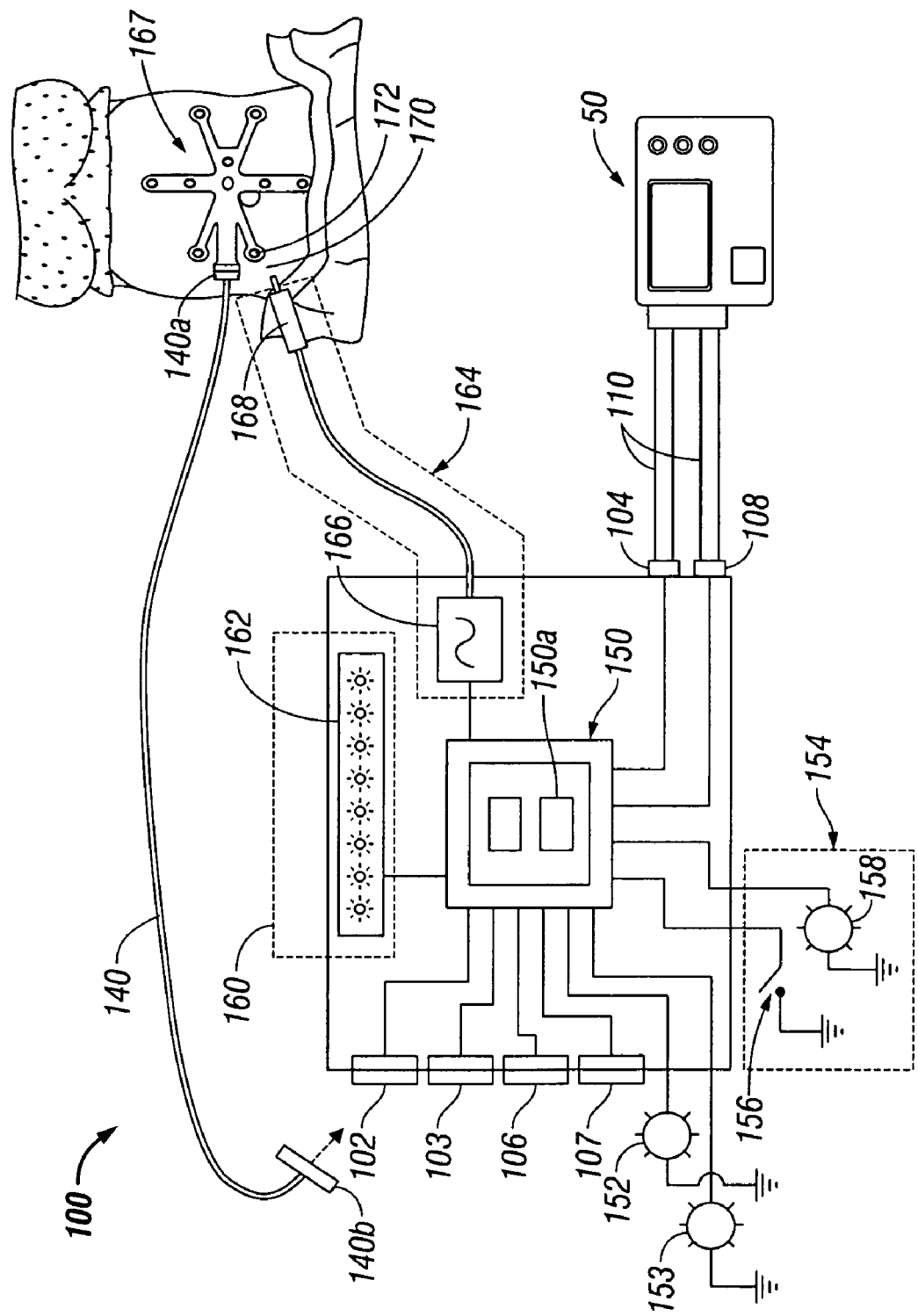
FIG. 3 is an electrical schematic illustrating the components of the cable monitoring apparatus.

FIG. 3 is a schematic of the cable monitoring apparatus 100 including signal processing circuitry 150 operably coupled to the various input connectors, output connectors, test connectors and indicator devices described hereinbelow. Signal processing circuitry 150 may include a Digital Signal Processor (DSP) 150A having a memory storing a set of programmable instructions capable of being executed by the DSP 150A for performing the functions described herein. Signal processing circuitry 150 may be an application-specific integrated circuit (ASIC) customized for this particular use or may be a general purpose device adapted for this use.

In the first mode of operation, signal processing circuitry 150 selectively passes monitoring information from the first and second input connectors 102, 106 to the respective first and second output connectors 104, 108. First and second output connectors 104, 108 pass monitoring information to display monitor 50. In this mode of operation, the monitoring information received at the display monitor 50 is essentially identical to the monitoring information received by the sensors 20, 30.

In the second mode of operation, signal processing circuitry 150 performs a diagnostic check on an electrical cable attached between the first or second input connectors 102, 106 and the respective first or second diagnostic connectors 103, 107. Signal processing circuitry 150 is connected to various indicators 152, 153 to indicate the results of the diagnostic check for each electrical cable. Diagnostic check may include testing the continuity and impedance of the various conductors, testing continuity and impedance between the various conductors, testing the capacitive properties of the cable, testing the insulation in the cable, measuring losses within the cable and conductors, measuring the frequency response and signal losses at various frequencies and any other test known in the art. Various indicators 152, 153 are indicative of at least one operating feature of the electrical cable which include test performed, or measurements made, on the cable. Indicators 152, 153 may be audible indicators, visual indicators, or other indicators known in the art.

The first or second input connectors 102, 106 may interface with various medical sensors (not shown) including a medical electrode, a medical electrode sensor array, an abdominal strain gage, a tocodynamometer, an intrauterine pressure catheter, and an ultrasound transducer.

One such sensor, the pressure catheter, is a common apparatus for measuring the uterine contractions of a maternal abdomen. Various pressure catheter components and systems are described in U.S. Pat. No. 5,566,680 to Urion et al. titled "Transducer-Tipped Intrauterine Pressure Catheter System", the contents of which are incorporated herein by reference. Referring to FIG. 1, the IUP catheter 30 is a type of pressure catheter that measures force applied to the pressure catheter by the patient P.

In monitoring fetal contractions with a pressure catheter it often becomes necessary or desirable to "zero" or "re-zero" the pressure catheter in situ. U.S. application Ser. No. 10/952,942 to Zaiken et al. titled "Intrauterine Pressure Catheter Interface Cable System", the contents of which are incorporated herein by reference, describes a pressure catheter and a zero/re-zero apparatus and method.

Referring again to FIG. 3, an alternative embodiment of the present disclosure includes zero/re-zero hardware 154. The signal processing circuitry 150 of the cable monitoring apparatus is operably connected to zero/re-zero selector 156 and zero/re-zero indicator 158. Clinicians initiate a zero/re-zero of the monitoring device 50 and the pressure catheter by depressing the zero/re-zero selector 156. The signal processing circuitry 150 short-circuits the output connector, corresponding to the pressure catheter, to ground thus creating a zero voltage signal to the monitoring device 50. The zero voltage signal is held for a predetermined period of time and clinicians are alerted that the output connector is short-circuited by a zero/re-zero indicator 158. The length of time the zero voltage signal is held must be sufficient for clinician to perform a zero/re-zero operation on the monitoring device 50, typically between 5 and 30 seconds.

In yet another embodiment, the cable monitoring apparatus includes an indicator circuit 160. At least one indicator 162, corresponding to a medical signal received by a input connector 102, 106, provides information about an operating feature of the medical signal. Indicators may identify the presence of uterine or fetal ECG activity Referring again to FIG. 3, indicators 162 may correspond to the number of electrodes on the electrode array 167 applied to the maternal abdomen 170. Indicator circuit 160 is operably connected to the signal processing circuitry 150 and the signal processing circuitry 150 may drive the indicators 162 with a signal indicative of at least one operating feature of the electrical cable 140. An operating feature of the electrical cable 140 may be associated with the functionality of the cable, the quality of the signal transmitted by the electrical cable, or a feature of the electrical cable or medical signal.

In yet another embodiment of the present disclosure, indicators 162 include lights driven by signals from the signal processing circuitry 150 wherein the signals are indicative of the functionality of an electrical cable. Indicator circuit 160 includes an array of indicator lights 162 with at least one indicator light corresponding to a medical sensor. Each individual indicator light may be driven with a signal proportional to the medical signal from the sensor or device. Clinicians can troubleshoot problems with an electrical cable 140, sensor or device containing sensors, such as an electrode array 167, by observing the array of indicator lights 162 on the cable monitoring apparatus 100.

Referring again to FIG. 3, in yet another embodiment, the cable monitoring apparatus includes a signal transmitter assembly 164 having a signal generator 166 and a signal applicator 168. Signal generator 166 generates and supplies a signature signal to the signal processing circuitry 150 and the signal applicator 168. The signature signal is a low energy signal with distinct and identifiable voltage and frequency characteristics. The signal applicator 168 is applied to patient skin 170 in close proximity to a medical device, such as an electrode 172 in an electrode array 167. Electrode 172 receives the signature signal and supplies the sensed information, including the signature signal, to the cable monitoring apparatus 100 through the electrical cable 140. The signal processing circuitry 150 receives the sensed information, including the signature signal, and processes the sensed information and signature signal. The DSP 150A of the signal processing circuit 150 may compare the received signature signal to the generated signature signal to determine the functionality of the circuit between the signal applicator 168 and the cable monitoring apparatus 100. Various factors which may affect the circuit include the conductivity of patient skin 170 adjacent the electrode, the connection between patient skin 170 and the electrode 172, the electrical cable 140 and the electrical cable connections 140A, 140B.

In yet another embodiment, the signal applicator 168 is integrated into the electrode array 167. In use, signature signal is transmitted on one conductor of electrical cable 140, applied to patient skin 170 by the signal applicator integrated into the electrode array and received by the plurality of electrodes 172 on the electrode array 167. The DSP 150A of the signal processing circuit 150 may compare the received signal to the generated signal to determine the functionality of the electrode array 167 and electrical cable 140. In the case where all electrodes are receiving a signature signal of poor quality DSP 150A may compare the plurality of received signals to determine if the poor signal is due to the signal applicator.

Figure 4:
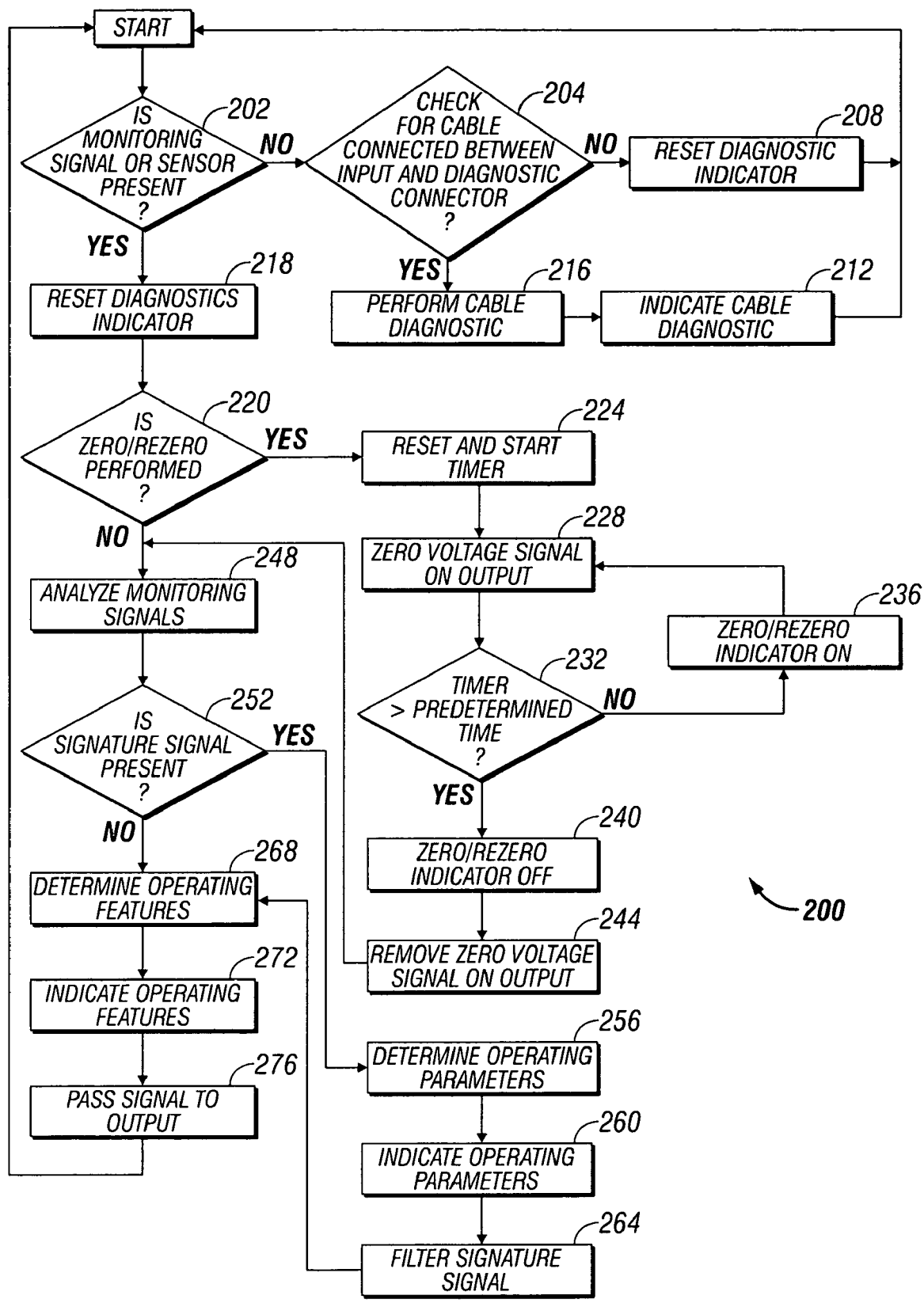
FIG. 4 is a programming flowchart illustrating functionality of the cable monitoring apparatus.

Referring now to FIG. 4, programming flowchart 200 illustrates processes executed by the DSP 150A for performing the functions described herein in accordance with the present disclosure. Cable monitoring apparatus may be configured in a first or second mode of operation prior to executing the steps and the mode of operation and connections may be modified at any time. While the programming flowchart of FIG. 4 includes multiple embodiments of the present disclosure, the steps executed by the DSP 150A may be limited to one or more of the various embodiment described herein.

Step 202 determines if a monitoring signal or sensor is present on an input connector. Various methods of detecting the presence of an input connector may be used such as measuring the impedance of the input or by analyzing the input signal. Sensors may also exhibit a distinct impedance characteristic or may contain a specific identification feature, such as a fixed resistor. Step 204 is executed if the signal or device is not detected on the input.

Step 204 checks for a cable connected between a input connector and a corresponding diagnostic connector. The presence of a cable between a input connector and a diagnostic connector may be determined by checking continuity, by a sensor detecting the physical presence of a cable or by user input. Step 208, which resets the diagnostic indicator, is executed if a cable is not detected between the input connectors. Step 216, which is executed if a cable is detected, performs cable diagnostic and the results of the diagnostics are indicated in Step 212.

Returning to Step 202, if a signal is detected on the input, the diagnostics indicator is reset in Step 218. The next step in sequence, Step 220, determines if the user has initiated a zero/re-zero function.

Zero/re-zero function is executed by Steps 224, 228, 232 and 236. Step 224 resets and starts the zero/re-zero timer. A zero voltage signal is held on the output in Step 228. If the zero/re-zero timer, in Step 232, has not exceeded the pre-determined time, the zero/re-zero indicator is turned on in Step 236, and the zero voltage signal is maintained on the output in Step 228. When the zero/re-zero timer exceeds the pre-determined time, the zero/re-zero indicator is turned off in Step 240, and the zero voltage signal is removed from the output in Step 244.

Returning to Step 220, if a zero/re-zero function is not performed, the monitoring signal at the input is analyzed in Step 248. The next step in the sequence, Step 252, checks for the presence of a signature signal in the monitoring signal. The clinician applies the signature signal transmitter to the patient (not shown in flow chart), in close proximity to the sensor, or to the sensor itself, in order to either check the functionality of the electrical cables and/or the electrical circuits. If the signature signal is present, Step 256 determines various cable and circuit parameters by comparing the received signature signal to the generated signature signal. Step 260 indicates at least one parameters indicative of the functionality of the electrical cable or circuit. Step 264 selectively filters the medical signal and removes at least a portion of the signature signal from the medical signal.

Next, in Step 268, the medical signal is analyzed to determine one or more operating features of the medical signal. At least one operating feature is indicated in Step 272 and the medical signal is passed to the output in Step 276.

In yet another embodiment, the features, functions and methods of the present disclosure, are incorporated into another electronic device, such as a personal computer, oscilloscope or monitoring device.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A cable monitoring apparatus for selectively passing medical signals to a medical monitoring apparatus, which comprises:
    a housing including at least one input connector adapted to electrically connect to a first end of a medical cable and at least one output connector adapted to electrically connect to a medical monitoring apparatus, the at least one input connector and the at least one output connector located on the housing of the cable monitoring apparatus;
    signal processing circuitry within said housing for receiving a medical signal from the medical cable via the at least one input connector and for selectively passing the medical signal to the medical monitoring apparatus via the at least one output connector when in a first mode of operation, and having application software for selectively testing functionality of the medical cable when in a second mode of operation and detached from a patient; and
    a cable diagnostic connector adapted to electrically connect with a second end of the medical cable, the second end being on an opposing end of the medical cable as the first end, whereby the signal processing circuitry tests the functionality of the medical cable when in the second mode of operation.

2. The cable monitoring apparatus according to claim 1, wherein the medical signal includes at least one monitoring signal selected from a group consisting of fetal medical signals and maternal medical signals.

3. The cable monitoring apparatus according to claim 2, wherein the at least one monitoring signal is generated from a medical device selected from a group consisting of at least one medical electrode, a medical electrode sensor array, an abdominal strain gauge, a tacodynamometer, an intrauterine pressure catheter, and an ultrasound transducer.

4. The cable monitoring apparatus according to claim 2, wherein the at least one monitoring signal is generated from a vacuum pressure sensor.

5. The cable monitoring apparatus according to claim 2, wherein the at least one monitoring signal is generated form a pulse oximeter.

6. The cable monitoring apparatus according to claim 2, wherein the at least one monitoring signal is generated from a pH sensing device.

7. The cable monitoring apparatus according to claim 2, wherein the at least one monitoring signal is generated from a sensor selected from a group consisting of a cervical dilation sensor, a cervical effacement sensor and a cervical length sensor.

8. The cable monitoring apparatus according to claim 2, wherein the at least one monitoring signal is generated from a fetal station sensor.

9. The cable monitoring apparatus according to claim 1, wherein said housing includes at least one indicator for indicating an operating parameter corresponding to functionality of the medical cable.

10. The cable monitoring apparatus according to claim 1, wherein said signal processing circuitry is adapted to process the at least one monitoring signal when in said first mode of operation and provides an output signal indicative of an operating parameter of the at least one monitoring signal.

11. The cable monitoring apparatus according to claim 10, wherein said output signal is of one of uterine activity or ECG activity.

12. The cable monitoring apparatus according to claim 11, wherein said housing includes an output signal indicator associated with said output signal for displaying a condition of said output signal.

13. The cable monitoring apparatus according to claim 12, wherein said output signal indicator is one of a visual or an audible alarm.

14. The cable monitoring apparatus according to claim 1, wherein said signal processing circuitry is configured to perform a zero I re-zero function wherein the at least one monitoring signal is short-circuited to create a zero voltage signal.

15. The cable monitoring apparatus according to claim 14, wherein said signal processing circuitry is adapted to short circuit the at least one monitoring signal for a predetermined period of time.

16. The cable monitoring apparatus according to claim 15, further comprising an indicator for indicating that the at least one monitoring signal is short-circuited.

17. The cable monitoring apparatus according to claim 1, further comprising a signature signal transmitter adapted to transmit a signature signal to a patient, said signature signal being identifiable by said signal processing circuitry for determining the functionality of the medical cable.

18. The cable monitoring apparatus according to claim 17, wherein said signature signal transmitter is selected from a group consisting of a wand, an electrode and a medical cable.

19. The cable monitoring apparatus according to claim 2 wherein the housing includes first and second input connectors for electrical connection to respective first and second medical cables.

20. A cable monitoring system comprising:
a cable monitoring apparatus for selectively passing at least one monitoring signal to a medical monitoring apparatus, the cable monitoring apparatus operable between a first and a second mode of operation wherein said first mode of operation selectively passes the at least one monitoring signal from a medical device through a medical cable and to the medical monitoring apparatus, and wherein said second mode of operation determines the functionality of the medical cable when detached from the medical device, and the cable monitoring apparatus including at least one input connector and at least one output connector located on a housing of the cable monitoring apparatus;
the functionality of the medical cable in the second mode of operation is determined by a diagnostic check wherein the diagnostic check is selected from a test that checks continuity of the medical cable, a test that measures an impedance property of the medical cable, a test that measures a capacitive property of the medical cable, a test that measures an insulative property of the medical cable, a test that measures a frequency response of the medical cable and/or a test that measures signal losses of the medical cable at one or more frequencies; and
a diagnostic input, whereby in the second mode of operation, a first end of the medical cable is connected to the at least one input connector and a second end of the medical cable is connected to the diagnostic input to thereby determine the functionality of the medical cable, wherein the first end and the second end are opposing ends of the medical cable.

21. The cable monitoring system according to claim 20, wherein the at least one monitoring signal is selected from a group consisting of fetal medical signals and maternal medical signals.

22. The cable monitoring system according to claim 20, comprising signal processing circuitry adapted to selectively pass the at least one monitoring signal from the medical device to the monitoring apparatus and to determine the functionality of the medical cable.

23. The cable monitoring apparatus according to claim 1, wherein the functionality of the medical cable in the second mode of operation is determined by a diagnostic check wherein the diagnostic check is selected from a test that checks continuity of the medical cable, a test that measures an impedance property of the medical cable, a test that measures a capacitive property of the medical cable, a test that measures an insulative property of the medical cable, a test that measures a frequency response of the medical cable and a test that measures signal losses of the medical cable at one or more frequencies.

24. The cable monitoring apparatus according to claim 1, wherein the at least one input connector and the at least one output connector are physically located on a surface of the housing of the cable monitoring apparatus such that there is no physical separation between the housing and the at least one input and output connectors.

25. The cable monitoring system according to claim 20, wherein the at least one input connector and the at least one output connector are physically located on a surface of the housing of the cable monitoring apparatus such that there is no physical separation between the housing and the at least one input and output connectors.

* * * * *